United States Patent [19]

Bauer et al.

[11] 4,158,610

[45] Jun. 19, 1979

[54] METHOD AND APPARATUS FOR DETERMINING AND CONTROLLING AMOUNT OF CARBON DEPOSITED ON A SURFACE BY A GAS

[75] Inventors: Edmund G. Bauer, Allentown; Glenn E. Shadle, Center Valley, both of Pa.

[73] Assignee: Bethlehem Steel Corporation, Bethlehem, Pa.

[21] Appl. No.: 890,890

[22] Filed: Mar. 28, 1978

[51] Int. Cl.$^2$ .................. C10B 57/18; G01N 27/04; H01C 1/00
[52] U.S. Cl. .................................. 201/1; 23/230 A; 23/230 PC; 23/232 E; 73/28; 202/270; 324/65 R; 324/65 CR; 324/71 R; 338/13; 338/34; 422/62; 422/68; 422/78; 422/98; 422/105; 422/119

[58] Field of Search .................. 201/1, 41; 202/270; 23/232 E, 254 E, 230 A, 230 PC; 324/65 R(U.S. only 1968 to date), 65 CR, 71 R(U.S. Only 1967 to date); 338/13, 34; 73/23(1971 to date); 55/274(U.S. Only 1973 to date); 422/62(U.S. Only), 83(U.S. Only), 78(U.S. Only), 98(U.S. Only), 108(U.S. Only), 68(U.S. Only 1975 to date), 105(U.S. Only 1974 to date), 119(U.S. Only 1975 to date)

[56] References Cited

U.S. PATENT DOCUMENTS

| 3,693,409 | 9/1972 | Yamagishi | 23/254 E X |
|---|---|---|---|
| 3,695,848 | 10/1972 | Taguchi | 23/254 E |
| 3,864,083 | 2/1975 | Green | 23/230 PC |
| 3,911,386 | 10/1975 | Beaudoin et al. | 23/254 E X |
| 4,033,169 | 7/1977 | Fujishiro et al. | 23/254 E X |

Primary Examiner—Joseph Scovronek
Attorney, Agent, or Firm—Joseph J. O'Keefe; Michael J. Delaney; Anson W. Biggs

[57] ABSTRACT

The amount of solid carbon deposited on a surface by a gas during the coking cycle in a coke oven is determined by measuring the thickness by electrical resistance readings, as a function of time, of carbon deposited on a probe passing through the roof of the oven and into the path of the gases flowing out of the oven.

3 Claims, 7 Drawing Figures

METHOD AND APPARATUS FOR DETERMINING AND CONTROLLING AMOUNT OF CARBON DEPOSITED ON A SURFACE BY A GAS

BACKGROUND OF THE INVENTION

This invention relates to measuring apparatus and method and more particularly to means for indicating the thickness of carbon deposition on a surface as a function of time.

In the manufacture of coke the formation of carbon on the upper walls and roof is a problem. The roof carbon deposits can develop to such a degree as to block charging holes, thus restricting the flow of coal and can also build so that a leveling bar cannot fit through the oven. Furthermore, hydrocarbon gases are released from the coal during the coking cycle. These hydrocarbon gases are removed from the coke oven and formed into useful byproducts, e.g., tar. However, at times the tar is characterized by a high content of solid carbon particles, thereby rendering the tar unsaleable. These particles are the result of entrained particles and thermal cracking of the hydrocarbon gases.

The two major parameters to roof carbon formation are (1) coal quality, and (2) oven top temperature. Of the two, coal may make the most important contribution to roof carbon formation but is not a condition that is easily changed or controlled. Oven top temperature is, on the other hand, more readily controlled and has a significant effect on the formation of roof carbon. If the heating is not controlled, uniform roof carbon formation can reach unmanageable proportions.

The current methods for controlling buildup of roof carbon are: (1) mechanical—i.e., carbon cutters on the ram head on all pushers, reduction of heat to top of the oven through flue system adjustments, and punching out plugged standpipes at oven roof level; (2) chemical—i.e., carrying one empty oven in the schedule and/or decarbonizing air sprays on the ram head.

Although these procedures are presently effective for control, roof carbon buildup now becomes the criterion for coking rate. Higher coking rates, made possible through improved heating and refractories, may be limited by roof carbon control.

In order to determine the effect of the coking process variables, e.g., BUT input/hour, oven roof temperature, gas flow rate from the oven, etc., it is desirable to measure the rate of deposition of the carbon, as a function of time, during the coking cycle.

SUMMARY OF THE INVENTION

It is, therefore, an object of this invention to provide apparatus for use in a coke oven to measure the rate of deposition of carbon as a function of time during a coking cycle.

It is a further object of this invention to provide a method for controlling carbon formation deposited on a surface by a gas.

The present invention accomplishes these objects by providing a unique probe inserted into the path of flow of gases in the free space above the coke in a coke oven, combined with an electronics package which provides for the plotting of the resistance sensed by the probe as a function of time on a recorder, e.g., a strip chart recorder.

DESCRIPTION OF THE PREFERRED EMBODIMENT

Figure 1:
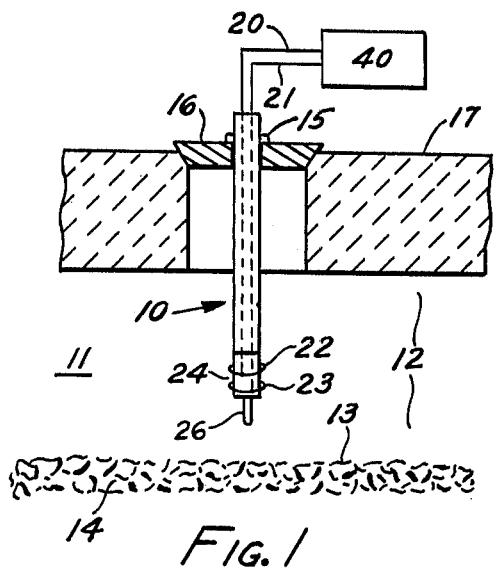
FIG. 1 is a general arrangement of the apparatus of the instant invention.

Referring now to the drawings and particularly to FIG. 1, the probe 10 of the instant invention is seen in place in coke oven 11 extending into the free space 12 above coal line 13 of the coal charge 14. Probe 10 is inserted through a fitting 15 in charging hole lid 16 in the coke oven roof 17. Lead wires 20 and 21 connect first and second spaced apart wires 22 and 23, respectively, encircling the measurement area 24 of the lower portion of probe 10 with electronics package 40 which is located remotely from the coke oven 11. The wires 22 and 23 serve as electrodes.

Figure 2:
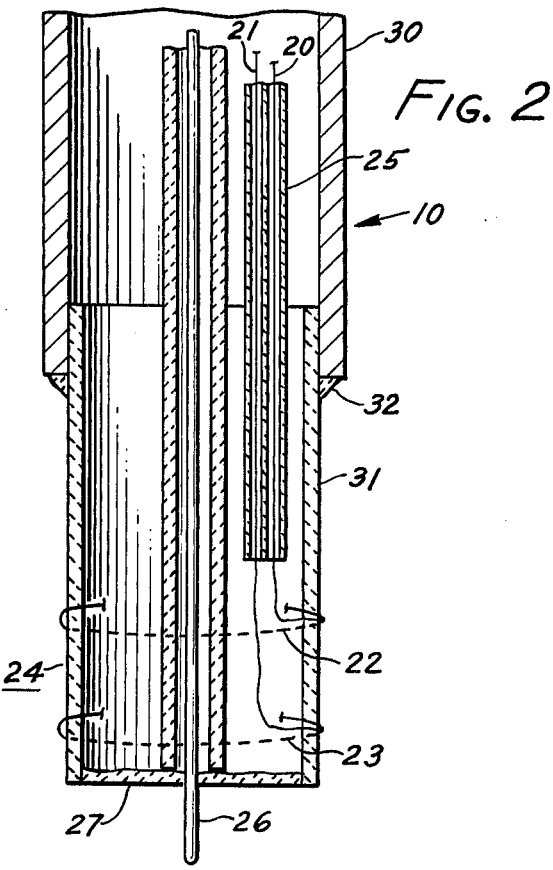
FIG. 2 is an enlarged fragmentary detailed drawing of the probe.

FIG. 2, to which particular reference is now made, is an enlarged fragmentary detail of probe 10. The probe 10 is a cylinder and comprises a ½ inch diameter stainless steel tube upper portion 30. The lower portion 31 is a 9.5 mm ceramic tube inserted into the lower end of the stainless steel tube upper portion 30 and is affixed thereto by ceramic cement as at 32 and extending downward therefrom approximately three inches. Spaced apart wires 22 and 23 are seen encircling the ceramic tube 31 in the measurement area 24 of the probe 10 and are connected by lead wires 20 and 21, respectively, to the electonics package 40 as seen in FIG. 1. The lead wires 20 and 21 are protected by a ⅛ inch, 2 hole ceramic insulator 25, each lead wire occupying one of the channels or holes through the tubular insulator 25. A 1/16 inch diameter sheathed type K thermocouple 26 is provided in probe 10 extending therethrough and protruding at the lower end thereof into the coke oven free space slightly to register the temperature of the gases therein. The lower end of the probe 10 is sealed by ceramic cement as at 27. The top of the probe 10 cylinder is also sealed.

Figure 4:
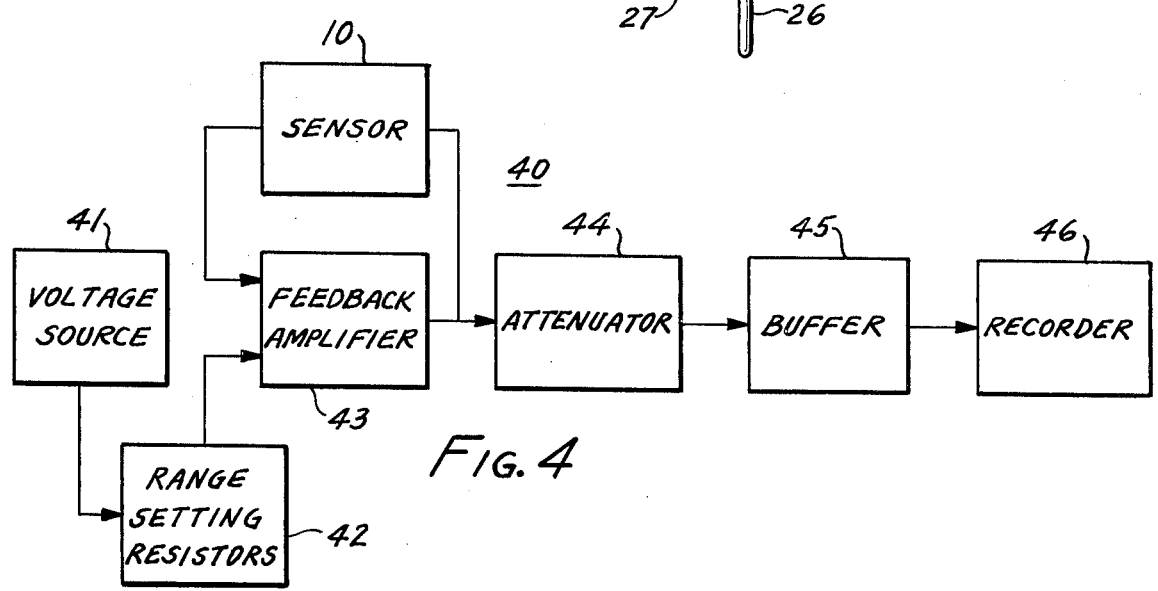
FIG. 4 is a block diagram showing the electronics package of the preferred embodiment.

The system for measuring the effective thickness of a layer of carbon deposited by a gas in a coke oven comprises the specially designed sensor or probe 10, signal processing electronics 40, and a standard voltage vs. time chart recorder 46, (FIG. 4).

The sensor or probe 10 is constructed entirely of materials designed to withstand the highly corrosive, high temperature environment of the coke oven. The dimensions and materials of the sensor or probe 10 shown in FIG. 2 are selected for system compatibility, although other combinations of dimensions would be suitable. The two spaced apart wires 22 and 23 located near the end of the sensor or probe 10 serve as the electrodes. The area between the electrodes 22 and 23 on the outside surface of the ceramic tube 31 comprises the measuring area 24 of the sensor 10. The electrical resistance between the two electrodes 22 and 23 is in excess of 10 million ohms, until the carbon formation begins. As carbon buildup occurs, the electrical resistance of the sensor decreases proportionately. The effective thickness of the carbon buildup is obtained from the slope of the resistance vs. time curve and other physical parameters described in the equation:

$$t = (\rho l / \pi D \beta T^X)$$

where
t = effective thickness of buildup
l = gage length of probe
D = diameter of probe
ρ = electrical resistivity of the carbon
β = measured electrical resistance of probe at time zero
T = time
X = slope of resistance-time curve.

The electronics package 40 as shown in FIG. 4 comprises voltage source 41, range setting resistors 42, feedback amplifier 43, attenuator 44, buffer 45 and recorder 46.

The signal processing electronics package 40 accepts the electrical resistance information from the sensor 10 and processes it for introduction to the recorder 46. A 5-volt signal is generated by the voltage source 41 and is supplied to the feedback amplifier 43 through the range setting resistors 42. These resistors 42 scale the 5-volt signal to provide a decade change of resistance in the system for each resistor step. The 5-volt level is selected to provide adequate signal to reduce the effect of electrical noise in the system. The switching of the range setting resistors 42 can be done manually or under the control of the recorder 46, as the probe or sensor 10 resistance changes decades. This feature enables high resistance sensitivity over the six decades of sensor resistance change. The signal input to the feedback amplifier 43 is amplified in proportion to the value of the sensor 10 resistance in the feedback circuit of the amplifier 43. Full scale recorder input results in all ranges when the resistance of the range setting resistor equals the sensor resistance. The purpose of the feedback amplifier 43 is to provide a relatively constant input loading for the recorder 46. The output of the feedback amplifier 43 is then attenuated to the level required for recorder operation, and buffered to match the input impedance of the recorder 46.

The recorder 46 is a standard potentiometric strip chart recorder which feeds chart paper at a calibrated rate and provides a continuous record of voltage vs. time on the chart.

Materials which can stand up to the temperatures, as high as 2000° F., and corrosive atmosphere of the coke oven free space 12 are essential. The probe 10 described herein uses platinum wire for those wires which are used for measurement purposes, e.g., electrodes 22 annd 23. Any high melting point material with a low electrical resistance may be used. Stainless steel is used for the structural sheath or upper portion of cylinder 30.

The material between the wires at the measuring section must have an electrical resistance that is infinite compared to the electrical resistance of carbon. For example, the ceramic material must have an electrical resistance greater than one million ohms. A ceramic material, e.g., alumina having 99.7% purity is used in the probe described hereinabove. A low purity alumina contaminates the platinum and could cause an increase in the electrical resistance of the platinum. All holes and the ends of the probe 10 must be sealed to prevent pyrocarbon from bridging the platinum lead wires 20 and 21.

The thermocouple 26 is used to determine the oven free space 12 temperature. This is useful in relating carbon formation to changes in operation variables. Once this relationship has been established, the operators can use free space temperatures as a quick spot check for potential roof carbon problems.

The probe is inserted into an empty oven through the lid of the coke oven charging hole and soaked to operating temperature prior to use, thereby optimizing the resistance of the carbon thickness probe. The oven to be studies is charged and immediately after charging, the probe is removed from the empty oven and inserted into the charged oven. The electronics and recorder are hooked up and the resistance and free space temperature are recorded throughout the entire coking cycle. The buildup of carbon can be determined from the expression:

$$t = \rho l / \pi D \beta T^X$$

where
t = effective thickness of buildup
l = gage length of probe
D = diameter of probe
ρ = electrical resistivity of the carbon
β = measured electrical resistance of probe at time zero
T = time
X = slope of resistance-time curve.

Changing process variables will influence ρ and X. Changing the probe will influence l, D, and β.

With the above equation, unique curves can be obtained for a particular slot oven run at a particular set of conditions.

Figure 3:
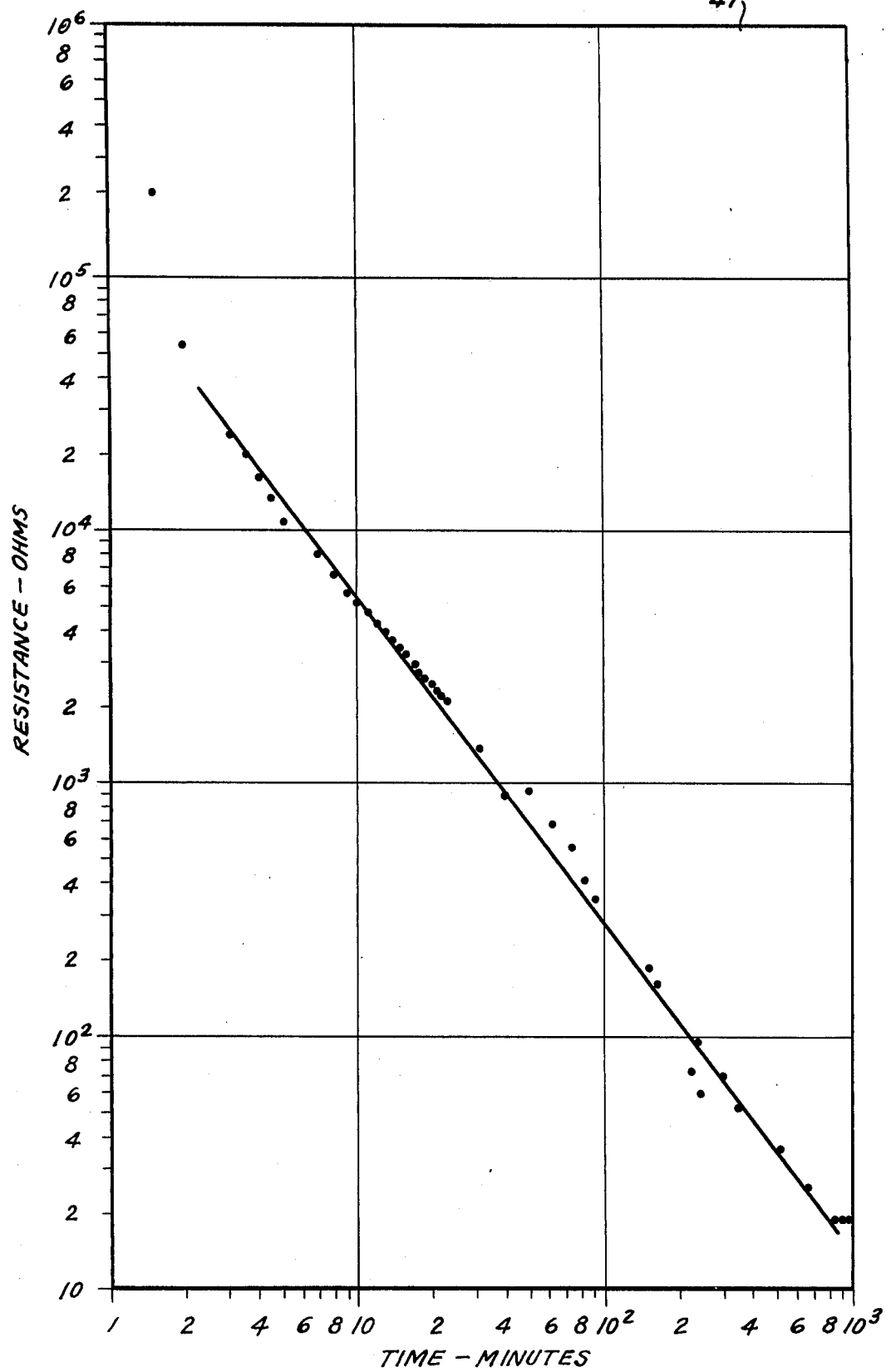
FIG. 3 is a typical time v. resistance chart developed through means of the instant invention.

In operation: An 18" test oven was charged with a typical coking coal mix, e.g., 70% high volatile, 30% low volatile. The probe of the instant invention was placed in a hot empty oven about an hour prior to charging of the test oven and soaked to a temperature of about 1600° F. A reading of probe resistance was made of the hot, clean probe prior to removal from the empty soaking oven. After the test oven was charged and the leveling operation completed the probe was pulled from the empty soaking oven and inserted through a fitting 15 in the charging hole lid 16. The probe 10 was connected to the electronics package 40 while still in the empty soaking oven. After insertion of the probe 10 into the test oven the strip chart recorder 46 was actuated. Initially the speed of the chart was 120 inches/hour in order to get a good trace on the chart during the period of large resistance change, about 20 minutes. After this initial 20 minute period the strip chart speed was reduced to 6 inches/hour and kept there for the duration of the coking cycle, approximately 18 hours. At the completion of the test period the strip chart was removed from the recorder 46 and the probe resistance values were read off of the chart at about 40 points. These points were plotted on a log-log graph 47 and the slope of the time vs. resistance curve was established thereby as shown on FIG. 3.

The effective buildup of carbon is determined by substituting the process variables and the data obtained from the strip chart in the formula hereinbefore referred to:

$$t = \rho l / \pi D \beta T^X$$

ALTERNATE EMBODIMENTS

Several alternative approaches exist for observing and/or controlling carbon formation on the sensor or probe 10.

Figure 5:
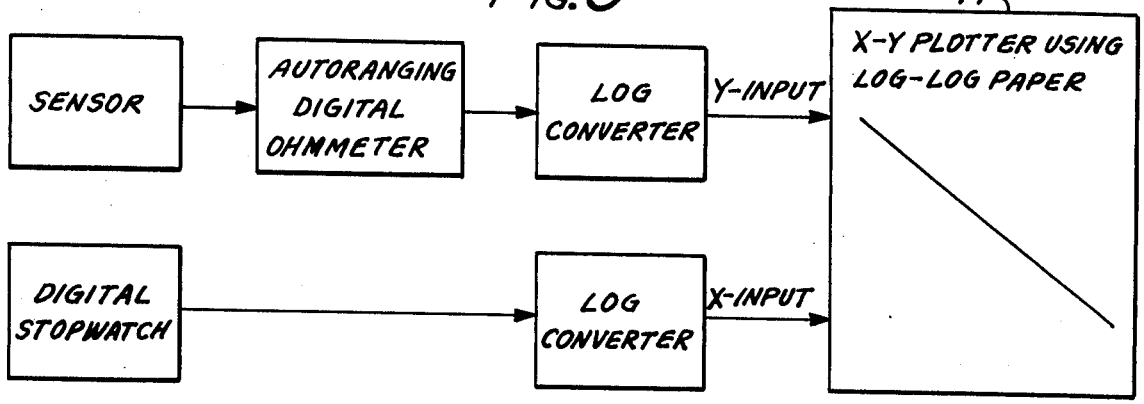
FIGS. 5 through 7 inclusive are block diagrams of alternate embodiments.

In the embodiment shown in FIG. 5 decreasing resistance of the carbon formation is sensed by the probe or sensor 10 and measured by an autoranging digital ohmmeter. Autoranging is required because of the 5-decade resistance changes of the probe or sensor 10. The analog voltage output from the ohmmeter is supplied to a logarithmic converter. The output of the converter becomes the Y input of an X-Y plotter 47'. The X-input to the plotter is obtained from the analog output of a digital stopwatch, which is also logarithmically converted. The resulting plot describes a straight line and actual resistance values at specific times can be read directly from the plot, when log-log paper is used for the plot. A coke oven operator can observe the straight line plot and manually adjust the fuel input to the oven when the slope changes or deviations from the straight line occur.

Figure 6:
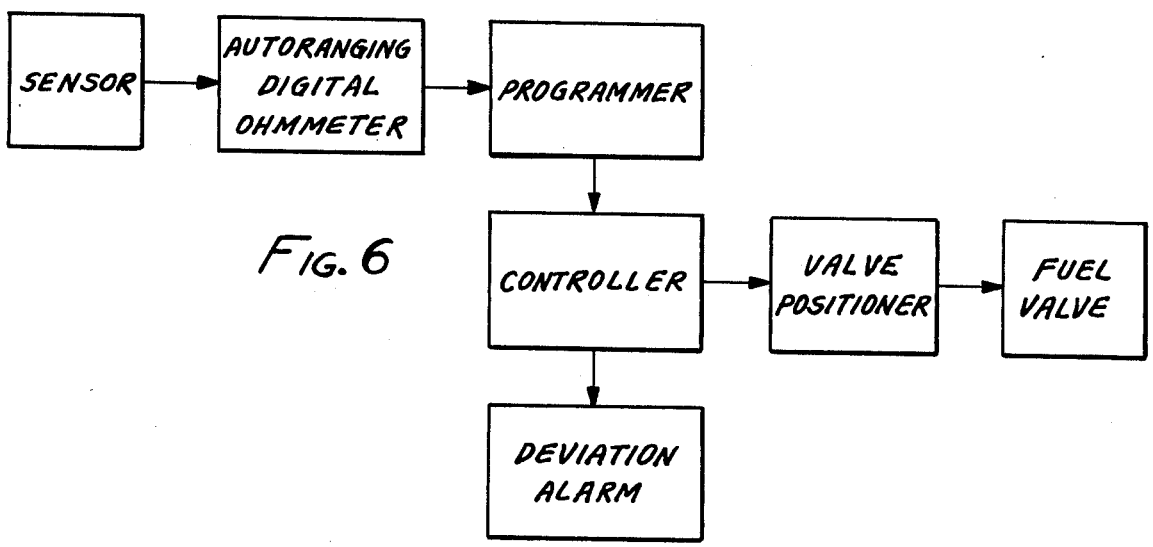

Referring now to FIG. 6 it is noted that as in the above configuration, the probe resistance is measured by an autoranging digital ohmmeter. The voltage output of the ohmmeter is used as an input signal to a programmer. The programmer compares the input signal in successive time increments with the programmed value desired for any time during the run. If a deviation exists between the input signal and the programmed value at a particular time, an error signal is generated. The error signal is applied to the controller which processes the signal for energizing an alarm, in the event of excess deviation. The controller also generates an output signal for use in making corrective action against the deviation such as driving a valve positioner, which in turn operates the fuel valve(s) for the coke oven.

Figure 7:
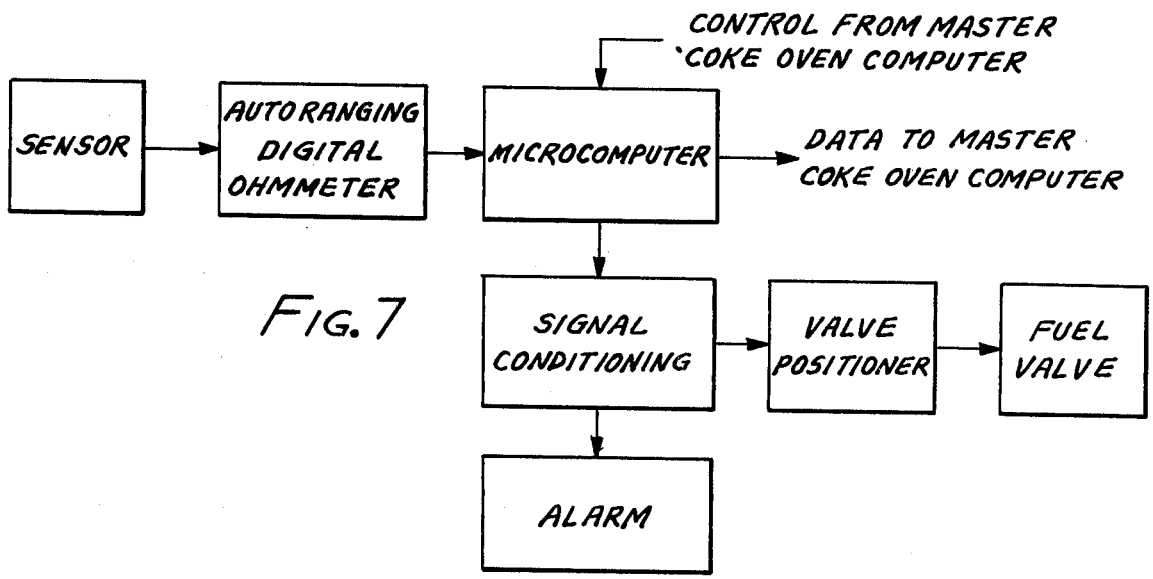

FIG. 7 depicts a computer controller oven operation. Probe resistance is measured again with an autoranging digital ohmmeter, the output of which is supplied to a microcomputer. The microcomputer maintains in its memory the information relating to probe resistance vs. time. Input information from the ohmmeter is continually compared to the stored data. Any deviation between the input data and the stored data produces an output from the microcomputer which can be used to take corrective action, energize alarms, or report the deviation to the master computer. The master coke oven computer can also instruct the microcomputer to initiate corrective action in response to other coke oven parameter changes.

The invention described hereinabove provides the method and apparatus to enable the effective thickness of a layer of carbon deposited by a gas on a surface to be determined. The apparatus comprises a cylinder having an outer surface which is characterized by extremely high resistivity, and which is disposed in the path of the flow of the gas with the axis of the cylinder being perpendicular to the direction of flow of the gas. First and second spaced apart wires encircle the cylinder in a plane perpendicular to the axis of the cylinder and serve as electrodes. The spaced apart wires are connected to an electric circuit or electronics package which is remotely located relative to the cylinder. Means is included in the electric circuit for plotting a curve of the resistance between the first and second wires as a function of time, e.g., a strip chart recorder 46, FIG. 4 or an X-Y plotter 47, FIG. 3.

Means which include a voltage source, sensor, range setting resistors, feedback amplifier, attenuator and buffer is also provided in the electric circuit for quantitatively measuring the resistance between the first and second wires where they encircle the surface to enable the thickness of a layer of carbon deposited on the surface to be calculated by means of the relationship:

$$t = \rho l / \pi D \beta T^X$$

where
- t = effective thickness of buildup
- l = gage length of probe
- D = diameter of probe
- $\rho$ = electrical resistivity of the carbon
- $\beta$ = measured electrical resistance of probe at time zero
- T = time
- X = slope of resistance-time curve.

We claim:

1. Apparatus to enable the effective thickness of a layer of carbon deposited by a gas on a surface to be determined, comprising:
   (a) a cylinder, the outer surface of which is characterized by extremely high resistivity, said cylinder being disposed in the path of the flow of said gas with its axis perpendicular to the direction of flow of said gas,
   (b) first and second spaced apart wires encircling said cylinder in a plane perpendicular to said axis,
   (c) said first and second spaced apart wires connected to an electric circuit remotely located relative to said cylinder, and
   (d) means included in said circuit for plotting a curve of the resistance between said first and second wires as a function of time and, for quantitatively measuring the resistance between said first and second wires where they encircle said surface to enable the thickness of a layer of carbon deposited on said surface to be determined by means of the relationship:

$$t = \rho l / \pi D \beta T^X$$

where
- t = the effective thickness of the carbon layer
- l = the distance between said first and second wires where they encircle said cylinder
- D = the outside diameter of said cylinder
- $\beta$ = the initial electrical resistance between said first and second wires where they encircle said cylinder
- $\rho$ = the resistivity of said carbon
- T = time
- X = the slope of the curve plotted by means (d) at time T.

2. A method for controlling the effective thickness of a layer of carbon deposited on a surface by a gas carrying entrained particles of carbon and by thermal cracking of said gas comprising the steps of:
   (a) providing a probe which is a cylinder having an outer surface characterized by extremely high resistivity and having spaced apart first and second wires therearound connected to an electric circuit,
   (b) positioning said probe with said cylinder being disposed in the path of the flow of said gas with its axis perpendicular to the direction of flow of said gas, (c) providing means in said electric circuit for plotting a curve of the resistance between the first and second wires as a function of time, (d) providing means for recording the temperature of said gas as a function of time, and (e) adjusting the temperature of said gas according to the slope of said curve.

3. The method according to claim 2 further including determining the effective thickness of a layer of carbon deposited on said surface by means of the relationship $$t = \rho l / \pi D \beta T^X$$

where
- $t$ = the effective thickness of the carbon layer
- $l$ = the distance between said first and second wires where they encircle said cylinder
- $D$ = the outside diameter of said cylinder
- $\beta$ = the initial electrical resistance between said first and second wires where they encircle said cylinder
- $\rho$ = the resistivity of said carbon
- $T$ = time
- $X$ = the slope of the curve plotted by means (c) at time T.

* * * * *